United States Patent
Lussier et al.

(10) Patent No.: US 7,399,857 B2
(45) Date of Patent: Jul. 15, 2008

(54) SYNTHESIS OF ORGANOMETALLIC CYCLOMETALLATED TRANSITION METAL COMPLEXES

(75) Inventors: Barbara B. Lussier, Rochester, NY (US); Joseph C. Deaton, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 273 days.

(21) Appl. No.: 11/289,040

(22) Filed: Nov. 29, 2005

(65) Prior Publication Data

US 2006/0223997 A1    Oct. 5, 2006

Related U.S. Application Data

(63) Continuation-in-part of application No. 11/095,164, filed on Mar. 31, 2005, now abandoned.

(51) Int. Cl.
*C07F 15/00*    (2006.01)

(52) U.S. Cl. ............ 546/2; 546/10; 548/108; 548/408; 556/136; 556/137

(58) Field of Classification Search ............ 546/2, 546/10; 548/108, 408; 556/136, 137
See application file for complete search history.

(56) References Cited

FOREIGN PATENT DOCUMENTS

WO    2004/043974    5/2004

OTHER PUBLICATIONS

J. C. Deaton, "Synthesis of Organometallic Cyclometallated Transition Metal Complexes", U.S. Appl. No. 10/879,657, (D-88247) filed Jun. 29, 2004.

*Primary Examiner*—P. Nazario Gonzalez
(74) *Attorney, Agent, or Firm*—Arthur E. Kluegel

(57) ABSTRACT

A process for forming a tris-cyclometallated complex comprises the step of reacting;
  a) an M(I) complex, wherein M represents Rh or Ir, and said complex comprises at least two ligands and contains at least two alkenyl groups pi-bonded to M, with
  b) a heterocyclic compound capable of forming a organometallic cyclometallated complex.

20 Claims, No Drawings

SYNTHESIS OF ORGANOMETALLIC CYCLOMETALLATED TRANSITION METAL COMPLEXES

CROSS REFERENCE TO RELATED APPLICATIONS

This is application is a continuation-in-part of application Ser. No. 11/095,164 filed Mar. 31, 2005, now abandoned, entitled Synthesis Of Organometallic Cyclometallated Transition Metal Complexes by Barbara B. Lussier and Joseph C. Deaton, which is incorporated herein by reference.

FIELD OF THE INVENTION

This invention relates to the field of organic synthesis and to a process for forming tris-cyclometallated organometallic complexes of the metals Ir (III) or Rh (III) from an intermediate complex.

BACKGROUND OF THE INVENTION

Organometallic cyclometallated complexes of transition metals (e.g. rhodium, iridium, platinum) have become useful materials because of their photophysical and photochemical properties. One especially important application of these compounds are as phosphorescent dopants in Organic Light-Emitting Diodes (OLEDs) because of their strong emission from triplet excited states (M. A. Baldo, et al, *Appl. Phys. Letters,* 75, 4 (1999)). An important class of phosphorescent cyclometallated complexes contain ligands that are at least bidentate wherein one coordination site of the ligand to the metal is through an N atom that is doubly bonded to C or another N atom, usually as part of a heterocyclic ring, and wherein another coordination site of the ligand to the metal is through a C atom. As used herein, the term "organometallic cyclometallated complex" means that at least one of the coordination sites forming the cyclic unit binding the metal atom by at least one ligand must be a metal-carbon bond. The metal-carbon bond is formed in place of a hydrogen-carbon bond of the free ligand before it is complexed. The carbon atom forming the metal carbon bond is usually also doubly bonded to another carbon as in, for example, a phenyl ring or a thienyl ring or furanyl ring. Further the carbon atom forming the metal-carbon bond also is preferably positioned so as to form a five- or six-membered metallacycle including the coordinated N atom of the ligand. A tris-cyclometallated complex has three such ligands. Some examples of iridium (III) organometallic cyclometallated complexes are shown below. It is also possible that the organometallic cyclometallating ligands are not all the same.

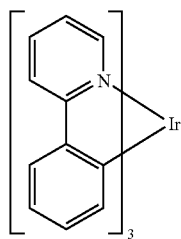

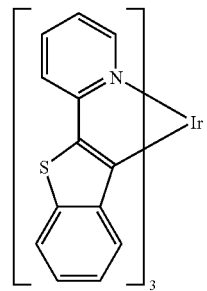

Further, there are two isomers, facial and meridional (fac and mer), possible for such complexes having three identical but unsymmetrical bidentate ligands as illustrated below. The facial isomers are typically more desirable in OLED applications because they usually have higher quantum efficiencies.

Fac

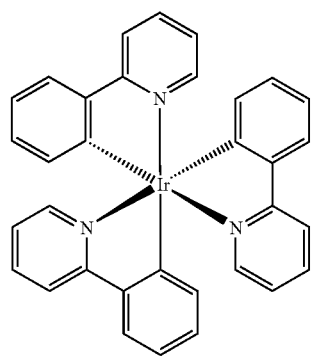

Mer

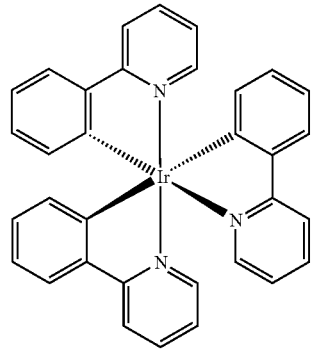

The usefulness and importance of organometallic cyclometallated complexes of second- and third-row transition metals have necessitated synthetic methods for preparing them more efficiently. Chassot et al., *Inorg. Chem.,* 23, 4249-4253, (1984), have used lithiated ligands with platinum compounds that include leaving groups to form cyclometallated complexes of the ligands with platinum. Jolliet et al., *Inorg. Chem.,* 35, 4883-4888, (1996) also used lithiated ligands to form cyclometallated complexes of the ligands with platinum or palladium, and Lamansky and Thompson, in WO 00/57676, used the same procedure for cyclometallated platinum complexes. These procedures suffer from low yields, as well as the relative instability of and difficulty in handling lithiated organic materials.

Organometallic cyclometallated complexes may also be formed from direct reaction of the cyclometallating ligand, wherein the carbon-hydrogen is activated and replaced by the carbon-metal bond. For example, fac-tris(2-phenylpyridinato-N,C$^{2'}$)iridium(III), or Ir(ppy)$_3$, was made by reaction of 2-phenylpyridine and tris(acetylacetonate) iridium (Ir(acac)$_3$) in glycerol solvent by K. Dedian et al., *Inorg. Chem.*, 30, 1685 (1991). Stössel and coworkers (WO02060910) further optimized and improved this reaction, but still using the expensive Ir(acac)$_3$ starting material. By reacting less expensive halide complexes of Ir(III) such as iridium(III) chloride hydrate with 2-phenylpyridine in a solvent comprising a 3:1 mixture of 2-ethoxy-ethanol and water, Nonoyama obtained dimeric organometallic cyclometallated complexes such as tetrakis(2-phenyl-pyridinato-N,C$^{2'}$-) (di-μ-chloro)di-iridium(III). (Ir(ppy)$_3$ was later extracted as a side product in 10% yield from this reaction mixture, K. A. King, et al., *J. Am. Chem. Soc.*, 107, 1431 (1985).) M. G. Colombo, et al., *Inorg Chem.*, 33, 545 (1994), further reacted the above-cited di-iridium complex with a silver salt in neat 2-phenylpyridine to obtain Ir(ppy)$_3$ in 75% yield. Grushin et al., US 2002/0190250, used this process to make additional tris-cyclometallated complexes of Ir(III) having fluorine-substitutions on phenylpyridine and phenylquinoline cyclometallating ligands. H. Konno and Y. Sasaki, *Chem. Lett.*, 32, 252 (2003) found that fac-Ir(ppy)$_3$ could be formed in good yield by the reaction of IrCl$_3$ 3H$_2$O with a excess of the ligand under microwave conditions. Many of these processes require a large excess of a ligand since it is employed as the solvent, thereby either consuming valuable material or necessitating a process to recover excess ligand.

Lamasky et al., *Inorg. Chem.*, 40, 1704-1711, (2001), demonstrated yet another process for making tris-cyclometallated iridium complexes. First, a mixed ligand complex, bis(7,8-benzoquinolinato-N,C$^{3'}$)iridium(III)(acetylacetonate), was made from tetrakis(7,8-benzoquinolinato-N,C$^{3'}$)(di-μ-chloro)di-iridium(III). Then the bis(7,8-benzoquinolinato-N, C$^{3'}$)iridium(III)(acetylacetonate) was reacted with additional 7,8-benzoquinoline in refluxing glycerol to produce a mixture of isomers of the tris-cyclometallated complex, tris(7,8-benzoquinolinato-N,C$^{3'}$)iridium(III). Kamatani et al., US 2003/0068526, have also employed this reaction type for additional cyclometallated iridium complexes. But this process often yields less desirable meridional isomers or mixtures of the facial and meridional isomers of the tris-cyclometallated complexes. This process also requires very long reaction times at elevated temperatures, in the case of many other desired ligands, to completely replace the acetylacetonate or similar anionic bidentate ligand with the desired organometallic cyclometallating ligand. Tamayo et al., *J. Am. Chem. Soc.*, 125, 7377-7387 (2003), have shown that reaction of dimeric organometallic cyclometallated complexes such as tetrakis(2-phenyl-pyridinato-N,C$^{2'}$) (di-μ-chloro)di-iridium (III) with sodium carbonate and additional cyclometallating ligand in glycerol can lead to formation of meridional isomers in many cases, while further reaction at higher temperatures results in formation of mostly facial isomer. However, this procedure is inconvenient for facial isomers as it necessitates finding exact conditions for the reaction of each ligand.

U.S. Pat. No. 6,870,054 describes a process for forming organometallic cyclometallated complexes of Ir(III) comprising the step of reacting a halide-containing complex of the metal with a silver salt and a heterocyclic organic ligand compound capable of forming an organometallic cyclometallated complex and in a solvent comprising an organic diol. However, this process fails or works poorly in many cases of desirable ligands. One of the possible reasons for this process not being generally applicable to a wide variety of possible cyclometallating ligands is that the solubility of the intermediate complexes may be too low in these solvents.

B. Schmid, F. Garces, and R. Watts, *Inorg. Chem.*, 33, 9 (1994), describe the preparation of solvento complexes of iridium that additionally comprise cyclometallating ligands. However these materials comprise cationic complexes that are not volatile enough for vapor deposition and therefore are not as useful as tris-cyclometallated complexes for OLED applications.

Commonly assigned U.S. Ser. No. 10/879,657, filed on Jun. 29, 2004, describes a process for forming organometallic tris-cyclometallated complexes of Ir(III) or Rh(III) from a complex comprising an Ir (III) or Rh (III) metal ion and two cyclometallated ligands, two monodentate ligands and a counterion. That process requires the formation of a bis-cyclometallated intermediate, which is difficult for certain ligands.

Nakayama and coworkers, WO 2004/043974, describe a process in which a monovalent iridium dinuclear complex, shown below, wherein A represents a non-conjugated diene compound and X represents a halogen atom, is reacted with a heterocyclic compound capable of forming an organometallic cyclometallated complex.

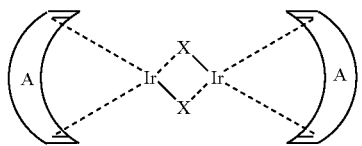

However, the product of this process is a dimeric organometallic cyclometallated complex such as tetrakis(2-phenyl-pyridinato-N,C$^{2'}$-) (di-μ-chloro)di-iridium(III), and not the desired tris-cyclometallated complex.

Despite the large number of investigations into the synthetic methodology for cyclometallated organometallic complexes, there remains a need for alternative methods that are applicable to a wide range of cyclometallating ligands, especially cyclometallating ligands containing multiple heteroatoms.

SUMMARY OF THE INVENTION

The invention provides a process for forming a tris-cyclometallated complex comprising the step of reacting;

a) an M(I) complex, wherein M represents Rh or Ir, and said complex comprises at least two ligands and contains at least two alkenyl groups pi-bonded to M, with b) a heterocyclic compound capable of forming a organometallic cyclometallated complex.

DETAILED DESCRIPTION OF THE INVENTION

The invention is summarized above. The process forms a tris-cyclometallated organometallic M(III) complex by reaction of an M(I) complex, wherein M represents a Rh or an Ir metal atom, and a heterocyclic compound capable of forming a cyclometallated organometallic complex. In one desirable embodiment, M represents Ir.

The M(I) complex includes at least two alkenyl groups pi-bonded to M. An alkene-metal bond involves overlap of an empty orbital of the metal with the pi cloud of the alkene. The metal is thus bonded to both carbons of the alkene. Illustrative examples of alkenyl groups are, a 1-propylene group, a 2-butene group, a cyclooctene group, a cycloheptene group, a vinyl acetate group, a styrene group and a 2-pentene group and fluorinated derivatives thereof. In one aspect of the invention, the two alkenyl groups pi-bonded to the metal are in the same ligand and thus form a diene, such as, for example, a 1,3-butadiene group, or a 1,5-hexadiene group. In another desirable embodiment, the two alkenyl groups comprise a cyclodiene group, such as a 1,5-cyclooctadiene group, a 1,4-cycloheptadiene group, a cyclooctatetraene group or a 2,5-norbornadiene group. In one suitable embodiment, the two alkenyl groups are not conjugated, for example, a 1,5-cyclooctadiene group or a 2,5-norbornadiene group.

Desirably the M(I) complex includes at least four alkenyl groups pi-bonded to M. In one embodiment, the four alkenyl groups include two independently selected diene ligand groups, such as two independently selected cyclodiene ligand groups. For example, the metal may be pi-bonded to two 1,5-cyclooctadiene groups or two 2,5-norbornadiene groups.

In an alternative embodiment, the M(I) complex is both pi-bonded to alkenyl ligands and to monodentate Lewis base ligands. Lewis base ligands are those capable of donating an electron pair. In one aspect, the M(I) complex contains two alkenyl ligands and two monodentate ligands. In another embodiment the monodentate ligands are not charged. Suitably the monodentate ligands are coordinated to the metal by means of nitrogen-metal or oxygen-metal or sulfur-metal bonds. For example, neutral monodentate ligands include nitriles, such as acetonitrile and propionitrile; sulfoxides, such as dimethylsulfoxide; amides such as dimethylformamide; ethers, such as tetrahydrofuran; water; amines, such as ammonia, piperidine, pyridine, and pyrazine; sulfur-donor ligands, such as thioethers, thiols, and thioureas. In one especially desirable embodiment the neutral monodentate ligand is a nitrile. A particularly suitable ligand is acetonitrile. When the metal is Rh(I), suitable ligands include phosphorous donor ligands such as triaryl or trialkyl phosphines.

In another embodiment, two neutral monodentate ligands may be joined to form a neutral bidentate ligand. Examples include ethylene diamine, bipyridyl, and phenanthroline. However, it is usually more desirable that the monodentate ligands are not joined because separate monodentate ligands may be more easily displaced from a complex than a bidentate ligand in the succeeding step of the invention process according to the principle of the chelate effect (J. E. Huheey, Inorganic Chemistry, 2$^{nd}$ ed., Harper & Row, New York, 1978, p. 481-487).

When the M(I) complex contains only alkenyl ligands or alkenyl ligands and neutral Lewis base ligands, the M(I) complex is cationic and requires an anionic counterion to balance the charge. Examples of suitable counterions include, for example, tetrafluoroborate and hexafluorophosphate.

When the M(I) complex contains alkenyl ligands and anionic Lewis base ligands, the M(I) complex is anionic and requires a cationic counterion to balance the charge. Examples of anionic ligands include hydroxide, alkoxides, phenoxides, thiocyanate, cyanate, and isocyanate. Examples of suitable counterions include sodium and tetrabutylammonium.

In one embodiment the M(I) complex is represented by Formula (1).

$$[(L^1)_n M(L^2)_m]X \qquad (1)$$

In Formula (1), M represents Ir(I) or Rh(I). Each L$^1$ represents an independently selected ligand comprising one alkenyl group pi-bonded to M. In one suitable embodiment, two L$^1$ groups join together to form a diene or cyclodiene ligand, each alkenyl group being pi-bonded to M. Each L$^2$ represents an independently selected Lewis base ligand. In one aspect of the invention, L$^2$ represents a monodentate ligand that is coordinated to the metal by means of a nitrogen-metal or an oxygen-metal bond, as described previously. Each L$^2$ may be the same or different. In Formula (1), n is 2-4; m is 0-2, provided in the case of an L$^1$ with two bonded alkenyl groups, that L$^1$ substituent counts as 2. The sum of n and m is four corresponding to four bonds to M. In one desirable embodiment n is 2, m is 2, and the two L$^1$ groups join to form a cyclodiene group, and each L$^2$ represents an independently selected monodentate ligand. In another suitable embodiment, n is 2, m is 0 and the L$^1$ groups join together so as to form two independently selected cyclodiene groups, for example two independently selected 1,4-cycloheptadiene groups or 2,5-norbornadiene groups.

X represents a counterion to balance the charge of the complex. In one suitable embodiment, X is an anionic group, such as tetrafluoroborate and hexafluorophosphonate. In one desirable embodiment, Formula (1) represents bis-(1,5-cyclooctadiene)iridium(I) tetrafluoroborate.

M(I) complexes, such as those represented by Formula (1), can be prepared by methods described in the literature. For example, see R. H. Crabtree, G. E. Morris, *J. Organomet. Chem.*, 135, 395 (1977); R. Uson, L. A. Oro, M. J. Fernandez, *J. Organomet. Chem.*, 193, 127 (1980); M. Dieguez, A. Ruiz, C. Claver, F. Doro, M. G. Sanna, S. Gladiali, *Inorg. Chim. Acta*, 357, 2957 (2004); and T. G. Schenck, J. M. Downes, C. R. C. Milne, P. B. Mackenzie, T. G. Boucher, J. Whelan, B. Bosnich, *Inorg. Chim.*, 24, 2334 (1985) and references cited therein. For example, some complexes represented by Formula (1) can be prepared from the compounds represented by Formula (A).

$$(L^1)_2 M(\mu\text{-}X)_2 M(L^1)_2 \qquad (A)$$

In Formula (A), M and L$^1$ were described previously. Each μ-X represents a bridging halide, such as Br or Cl. Complexes of Formula (A) may be prepared by literature methods, see for example, R. H. Crabtree, G. E. Morris, *J. Organomet. Chem.*, 135, 395 (1977). Reaction of compound (A) with a ligand in a suitable solvent, such as methylene chloride, can result in the formation of complexes of Formula (1). A silver salt, such as silver tetrafluoroborate or silver trifluoromethane sulfonate, is often added to promote displacement of the bridging halide from the complex of Formula (A).

Illustrative examples of Formula (1) compounds are listed below.

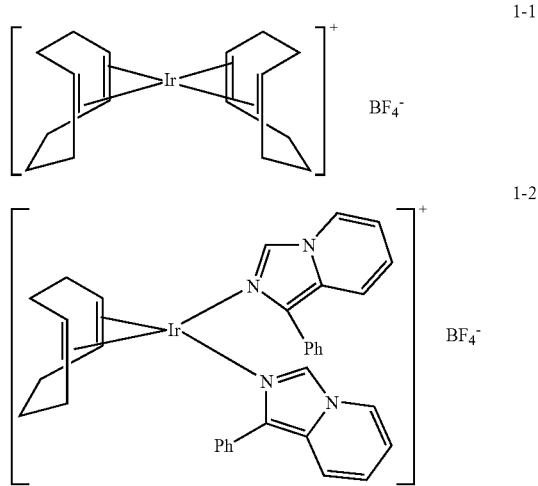

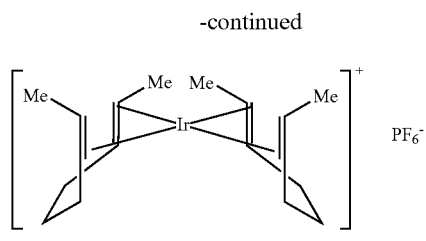
1-3
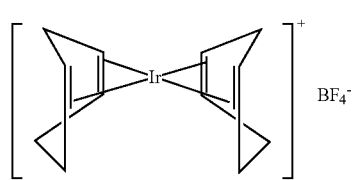
1-4
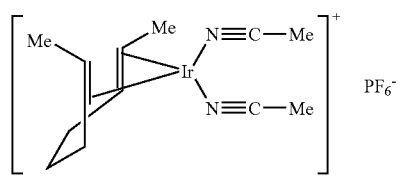
1-5
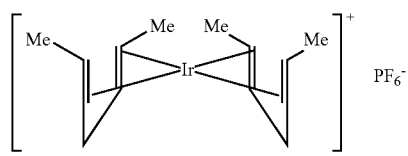
1-6
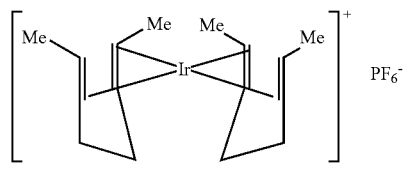
1-7
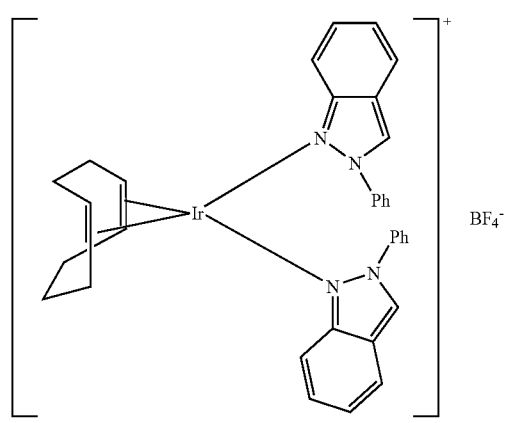
1-8
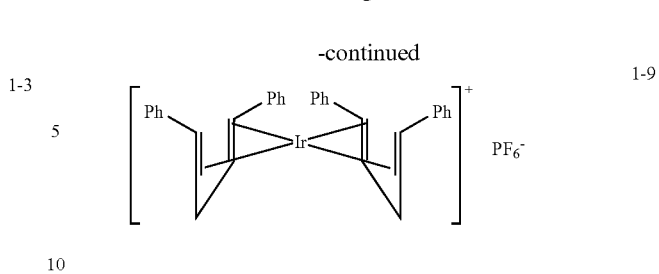
1-9
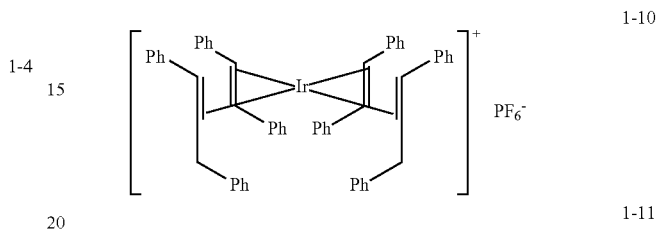
1-10
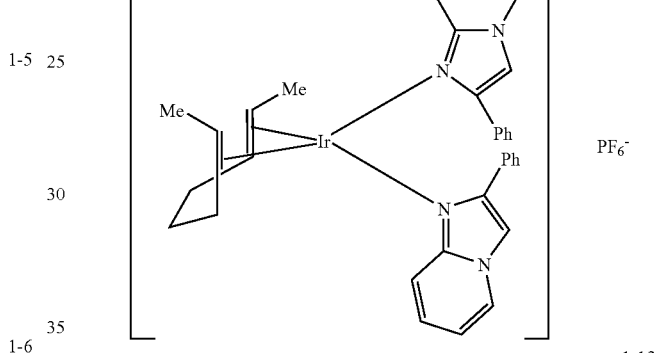
1-11
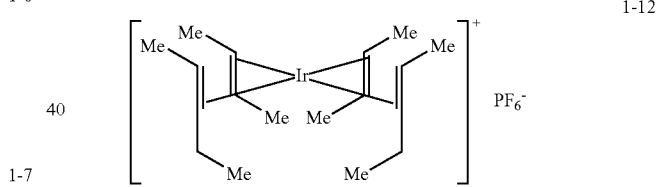
1-12
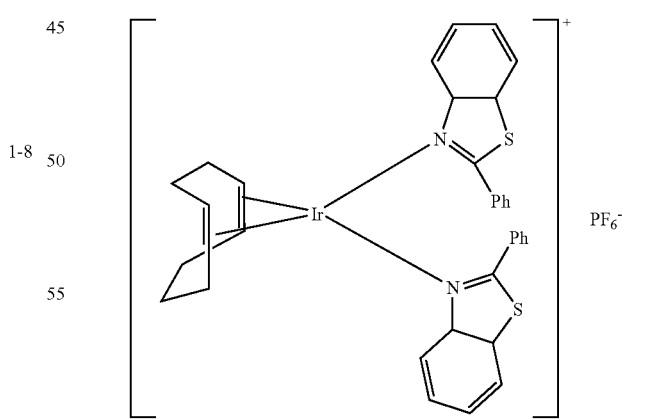
1-13
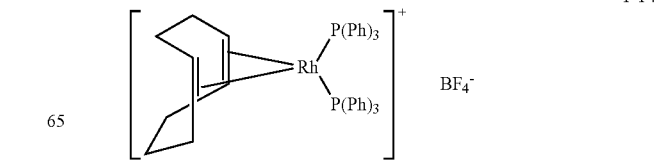
1-14

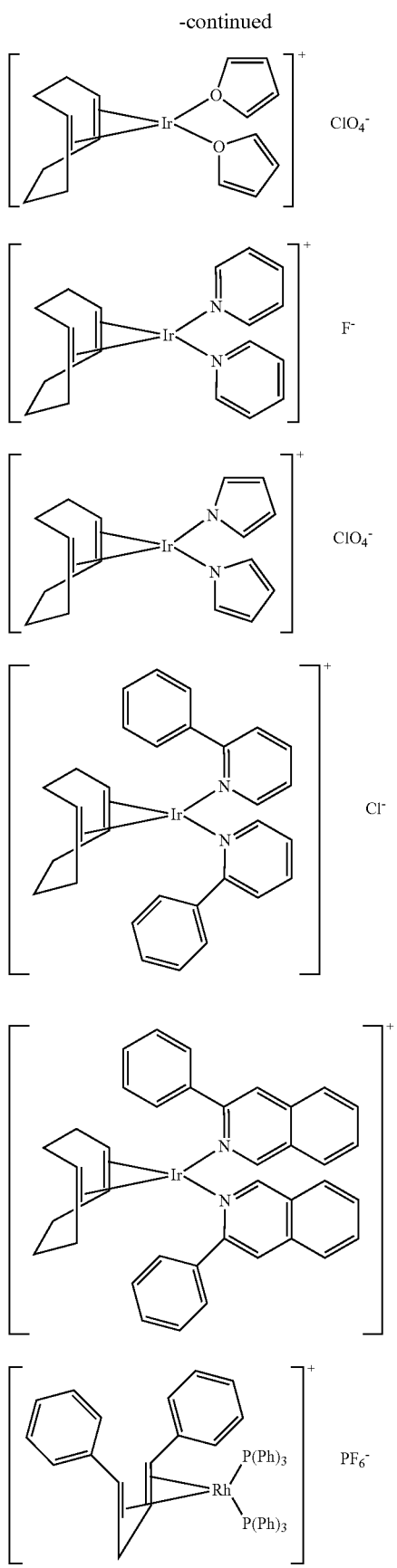
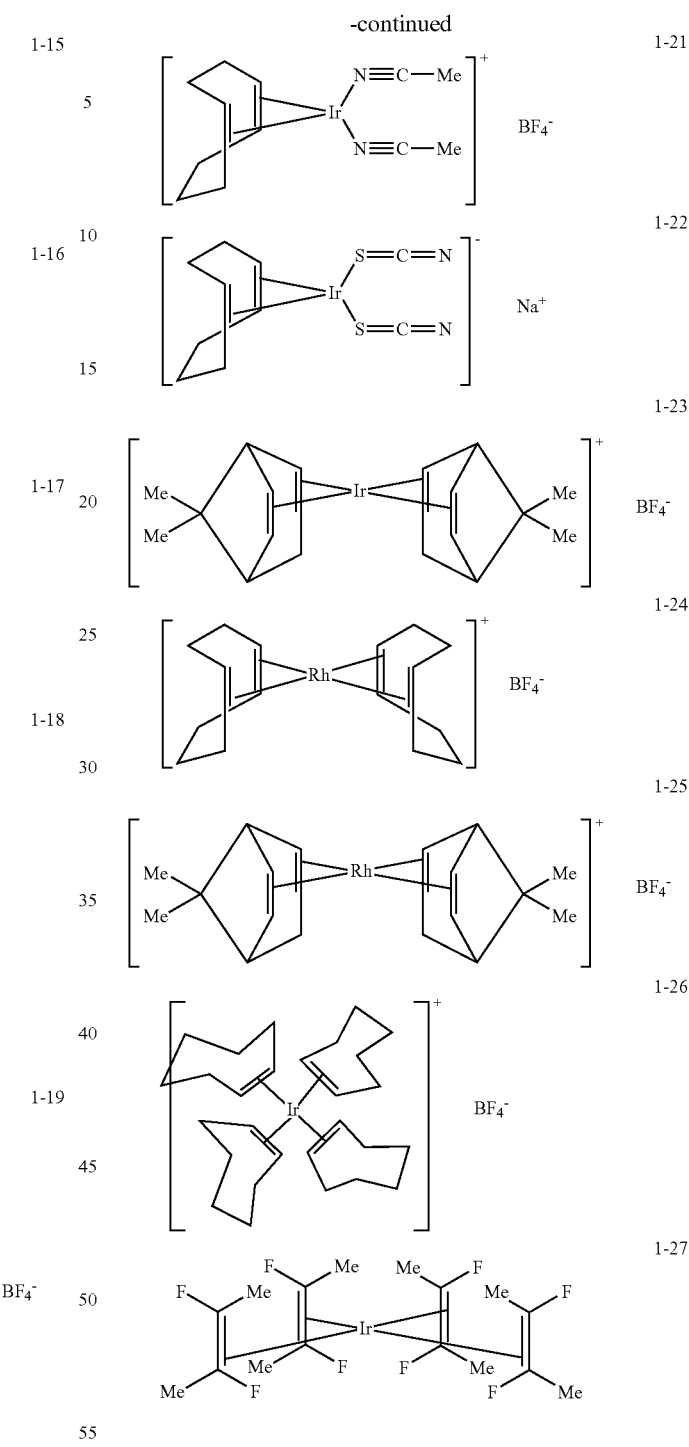

In the current process, the M(I) complex is reacted with a heterocyclic compound capable of forming a organometallic cyclometallated complex. As described previously, a cyclometallating ligand is a ligand with one available coordination site to coordinate to the metal through an N atom that is doubly bonded to C or another N atom, usually as part of a heterocyclic ring, and wherein another coordination site of the ligand is available to coordinate to the metal through a C atom, forming a metal-carbon bond. Formation of a cyclometallated complex is most favored when the resultant metal-containing cyclic unit is a five- or six-membered ring, especially a five-membered ring. In one embodiment the heterocyclic compound includes a pyridine group, a quinoline group, an isoquinoline group, a pyrimidine group, an indole group, an indazole group, a thiazole group, an oxazole group, an imidazole group, or a pyrazole group. Illustrative examples include a substituted or unsubstituted 2-phenylpyridine group, a 1-phenyl isoquinoline group, a 3-phenyl isoquinoline group, a 2-phenyl-quinoline group, and a 7,8-benzoquinoline group. In another embodiment, the heterocyclic compound contains at least two heteroatoms, such as a diazole group, a thiazole group, or an oxazole group. In one desirable embodiment, the heterocyclic compound includes a diazole group that has a fused aromatic ring group including a nitrogen of the diazole as a bridgehead nitrogen.

In one suitable embodiment the heterocyclic compound is represented by Formula (2a).

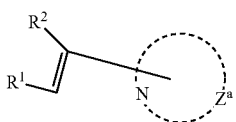
(2a)

In Formula (2a), $Z^a$ represents the atoms necessary to form an aromatic ring. $R^1$ and $R^2$ represent substituent groups, for example methyl groups or phenyl groups. $R^1$ and $R^2$ may combine to form a ring group. In one desirable embodiment, $R^1$ and $R^2$ combine to form an aromatic ring group, for example, a benzene ring group, a naphthalene ring group, a furan ring group, a thiophene ring group, or a benzothiophene ring group.

In another suitable embodiment the heterocyclic compound is represented by Formula (2b).

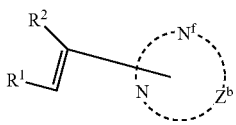
(2b)

In Formula (2b), $R^1$ and $R^2$, were described previously. $Z^b$ represents the atoms necessary to form a diazole ring group that is fused with at least one aromatic ring group. $N^f$ represents a nitrogen atom at a bridgehead position between the diazole ring group and the fused aromatic ring group;

Illustrative examples of cyclometallating ligands are listed below.

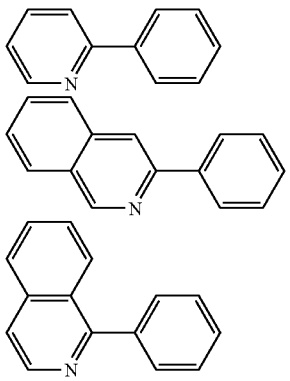

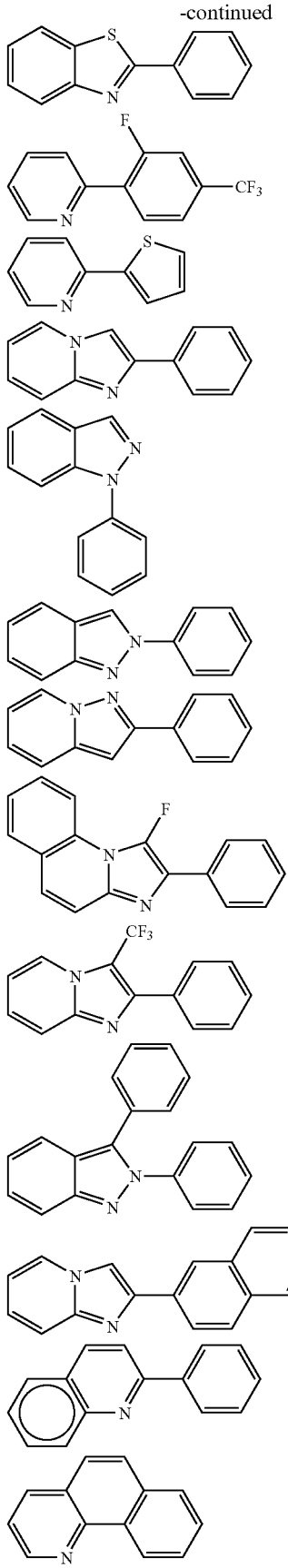

-continued

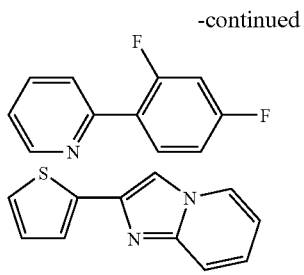

The M(I) complex is reacted with a ligand capable of forming an organometallic cyclometallated complex. In one suitable embodiment excess ligand is added and the excess ligand functions as a solvent for the reaction. More desirably, an additional solvent is used. Useful solvents include aliphatic alcohols, glycerol, aliphatic diols, aromatic alcohols and diols, aromatic esters and ethers. Desirably, the solvent comprises an aliphatic diol or an aromatic ester. Illustrative examples of solvents useful in the invention include 1-propanol, 2-ethoxy ethanol, phenoxyethanol, glycerol, ethylene glycol, 1,2-propanediol, 1,3-propanediol, 1,3-butanediol, and phenyl acetate.

The reaction mixtures may be conveniently heated to the reflux temperature of the solvent, or may be held in a constant temperature bath. A suitable temperature range for the reactions is 40 to 250° C. but more commonly is 140 to 220° C. or conveniently 150-190° C.

The process is carried out for a sufficient length of time to produce substantial amounts of the tris-cyclometallated complex. Suitable reaction times can be determined by monitoring the reaction. For example, by removing aliquots of the reaction mixture periodically and by using thin-layer-chromatography (TLC) or high-performance-liquid chromatography (HPLC) analysis one can determine the amount of reactants present, e.g., unreacted materials of Formula (1), and one can determine the amount of product formed. In this manner the progress of the reaction can be monitored. Typically the reaction times are 1 to 24 h, but may be shorter or longer.

Suitably the tris-cyclometallated product can be isolated and purified if necessary. Purification can be done by well-known methods such as sublimation, crystallization or column chromatography.

In one desirable embodiment, the M(I) complex represents bis-(1,5-cyclooctadiene)iridium(I) tetrafluoroborate. This compound can act as a common intermediate in the formation of tris-cyclometallated iridium complexes. Heating bis-(1,5-cyclooctadiene)iridium(I) tetrafluoroborate with excess amount of a ligand that is a heterocyclic compound capable of forming a organometallic cyclometallated complex, in a suitable solvent, such as 1,2-propanediol, can form the desired tris-cyclometallated complex. In most cases, the product precipitates from the reaction and is filtered, washed with pentane and dried. In some case, with certain less soluble ligands, an intermediate Ir(I) (1,5-cyclooctadiene) (ligand)$_2$ complex may precipitate. In this type of complex, the heterocyclic ligand is often not yet cyclometallated but coordinated only through N as a neutral mondentate ligand. This stable solid can be isolated, suspended in 1,2-propanediol or other suitable solvent with excess ligand, and heated to produce the tris-cyclometallated product.

In another embodiment, the M(I) complex again represents bis-(1,5-cyclooctadiene)iridium(I) tetrafluoroborate and this material is heated with a labile Lewis-base ligand, such as acetonitrile or tetrahydrofuran. This forms an intermediate complex, such as [Ir(I)(1,5-cyclooctadiene)(CH$_3$CN)$_2$][BF$_4$] or [Ir(I)(1,5-cyclooctadiene)(THF)$_2$][BF$_4$], which can be converted to a tris-cyclometallated iridium complex by heating it with a ligand that is a heterocyclic compound capable of forming an organometallic cyclometallated complex, in a suitable solvent, such as 1,2-propanediol.

In one suitable embodiment, the tris-cyclometallated product is represented by Formula (3a).

$$M'(L^3)(L^4)(L^5) \tag{3a}$$

In Formula (3a), M' represents Ir(III) or Rh(III) and $L^3$, $L^4$, and $L^5$ represent bidentate cyclometallating ligands which may be the same or different. In one desirable embodiment the ligands are the same. In an alternative embodiment, $L^3$ and $L^4$ represent the same ligand and $L^5$ represents a different ligand.

In another suitable embodiment the bidentate cyclometallating ligands comprise a 2-phenylpyridine group, a 1-phenylisoquinoline group, a 3-phenylisoquinoline group, a 1-phenylimidazo[1,2-a]pyridine, a thiazole ring group that is fused with at least one aromatic ring group, or an oxazole ring group that is fused with at least one aromatic ring group.

In another appropriate embodiment, the tris-metallated complex formed is represented by Formula (3b). In Formula (3b), M', $Z^b$, $N^f$, $R^1$ and $R^2$ were described previously.

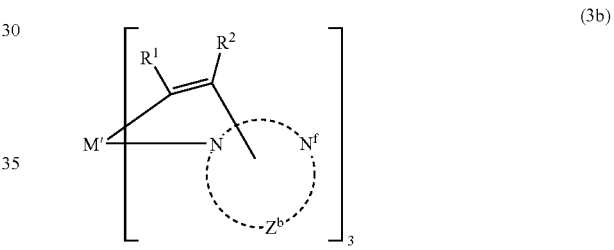

(3b)

In further embodiment, the tris-cyclometallated complex formed is represented by Formula (3c). In Formula (3c), M', $Z^b$, $N^f$, $R^1$ and $R^2$ were described previously.

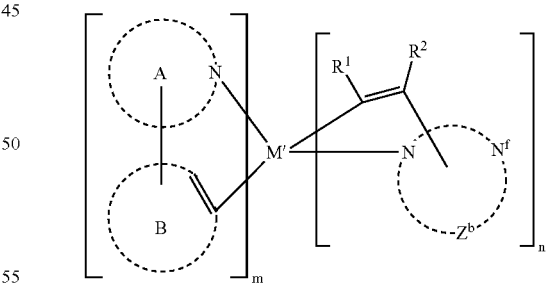

In Formula (3c), A represents a substituted or unsubstituted heterocyclic ring group containing at least one nitrogen atom, such as a pyridine ring group or a quinoline ring group.

In the Formula, B represents a substituted or unsubstituted aromatic or heteroaromatic ring. Examples of B include a phenyl ring group and a thienyl ring group. In one suitable embodiment, B represents an aryl group.

In the Formula, m is an integer from 1 to 3; and n in an integer from 0 to 2 such that m+n=3. In one desirable embodiment, m is 2 and n is 1.

Illustrative examples of tris-cyclometallated compounds are listed below.
3-1
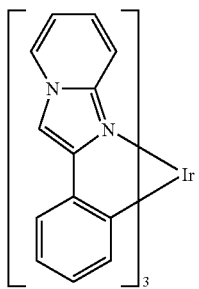
3-2
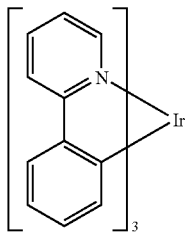
3-3
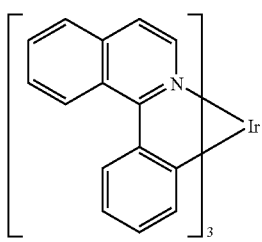
3-4
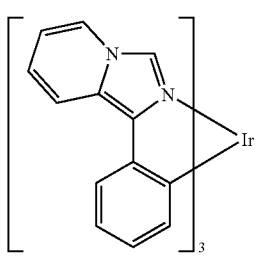
3-5
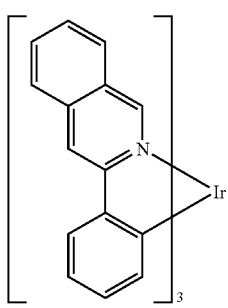
3-6
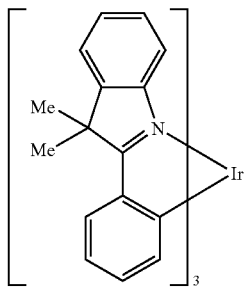
3-7
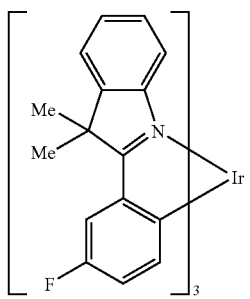
3-8
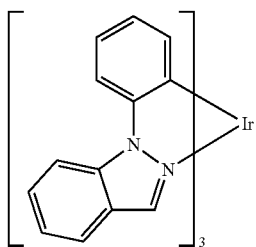
3-9
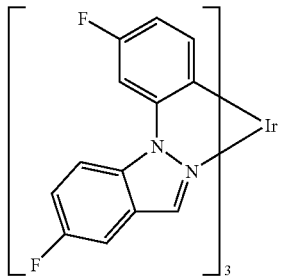

-continued
3-10
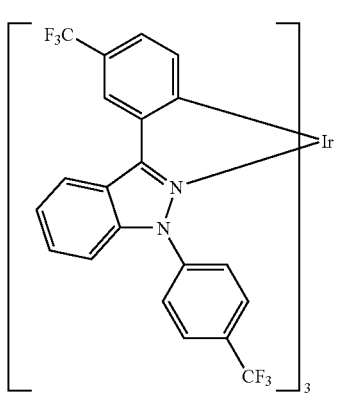
3-11
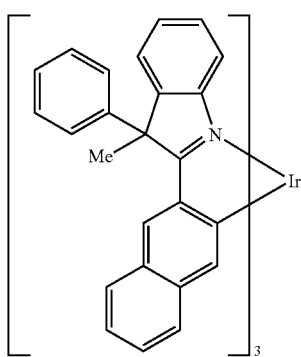
3-12
3-13
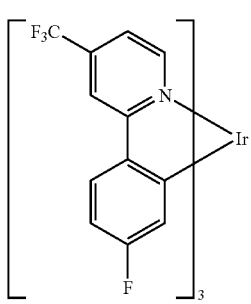
3-14
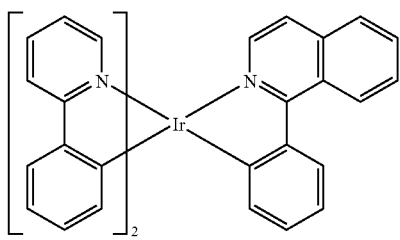
3-15
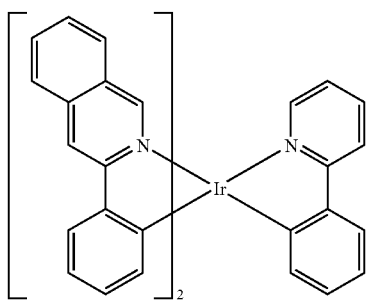
3-16
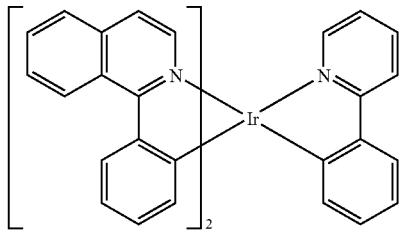
3-17
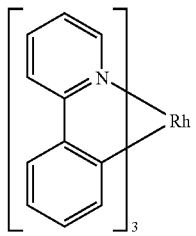
3-18
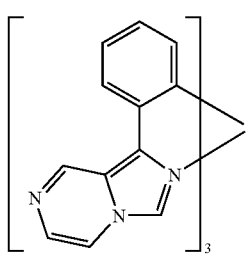

-continued
3-19
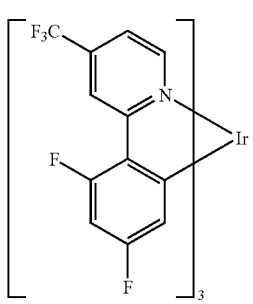
3-20
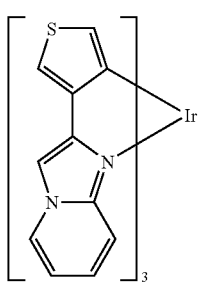
3-21
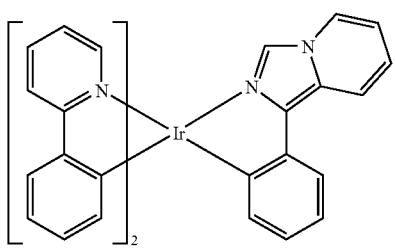
3-22
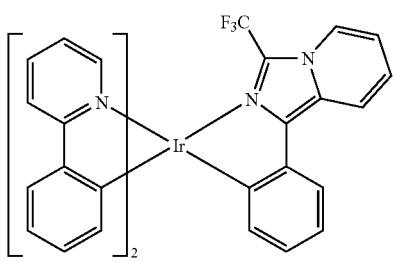
3-23
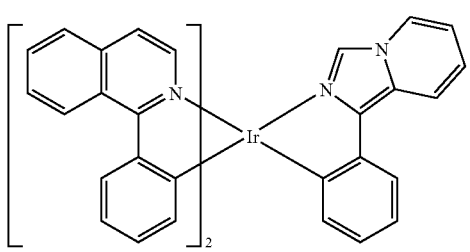
-continued
3-24
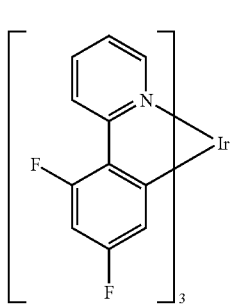
3-25
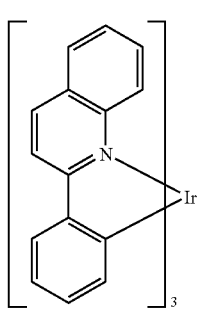
3-26
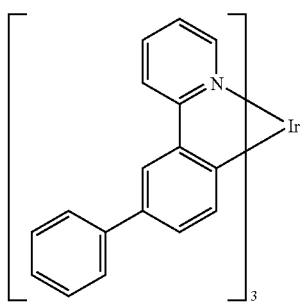
3-27
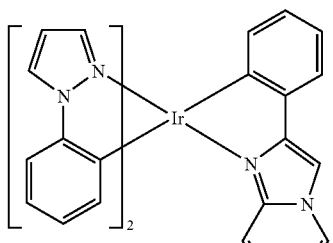

-continued

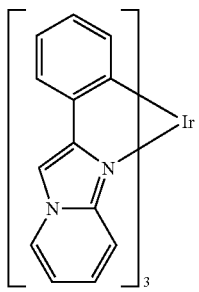

3-28

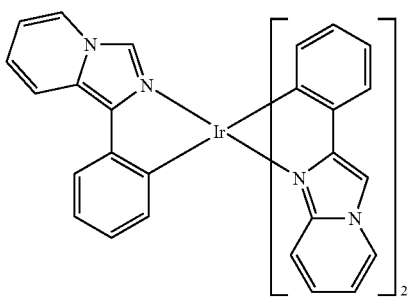

3-29

Embodiments of the invention may provide convenient methods of synthesis, employ relatively inexpensive starting materials and solvents, allow shorter reaction times, lower reaction temperatures, and be applicable to a wide range of cyclometallating ligands, especially cyclometallating ligands containing multiple heteroatoms. Embodiments may also provide higher yields of tris-cyclometallated complexes having fewer impurities. In addition embodiments may provide tris-cyclometallated complexes that have a high percentage of the desirable facial isomer, such as greater than 95% facial isomer or even greater than 99% facial isomer.

The invention and its advantages can be better appreciated by the following examples.

EXAMPLE 1

Preparation of fac-tris(2-phenylimidazopyridinato-N, $C^{2'}$)iridium(III) (3-1)

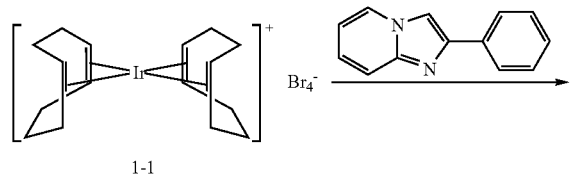

(eq. 1)

-continued

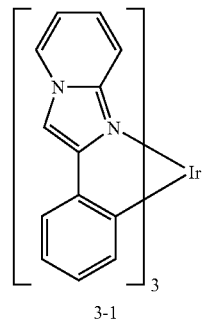

3-1

Complex 3-1 was prepared as shown in equation (1). Bis (1,5-cyclooctadiene)iridium(I) tetrafluoroborate (1-1) was prepared according to the procedure of T. G. Schenck, J. M. Downes, C. R. C. Milne, P. B. Mackenzie, T. G. Boucher, J. Whelan, B. Bosnich, *Inorg. Chim.*, 24, 2334 (1985). All solvents were dried and degassed. Reactions were run under a nitrogen atmosphere.

Bis(1,5-cyclooctadiene)iridium(I) tetrafluoroborate (0.68 g, 1.37 mmol) and 2-phenylimidazo[1,2-a]pyridine (1.3 g, 6.7 mmol) were taken up in 1,2-propanediol (25 mL) and the mixture freeze/thaw degassed. The mixture was heated to 50° C. for 20 min. under a nitrogen atmosphere. The temperature was slowly raised to 180° C. over a period of 2 hours and held at 180° C. for 20 min. The mixture was cooled to room temperature and the precipitate collected and washed with cold methanol. The solid was dried in vacuo to yield 0.94 g (89% yield, 99% pure by HPLC analysis). Analysis by matrix assisted laser desorption/ionization (MALDI) time-of-flight (TOF) mass spectrometry (m/e 772) and by $^1$H-nmr spectroscopy confirmed that this material was fac-tris(2-phenylimidazopyridinato-N,$C^{2'}$)iridium(III).

EXAMPLE 2

Preparation of fac-tris(1-phenylimidazopyridinato-N, $C^{2'}$)iridium(III) (3-4)

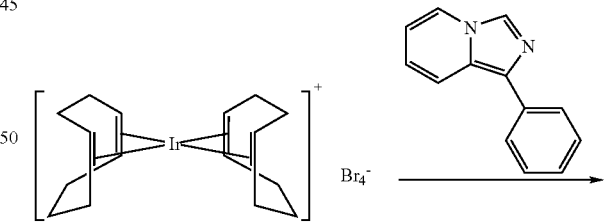

(eq. 2a)

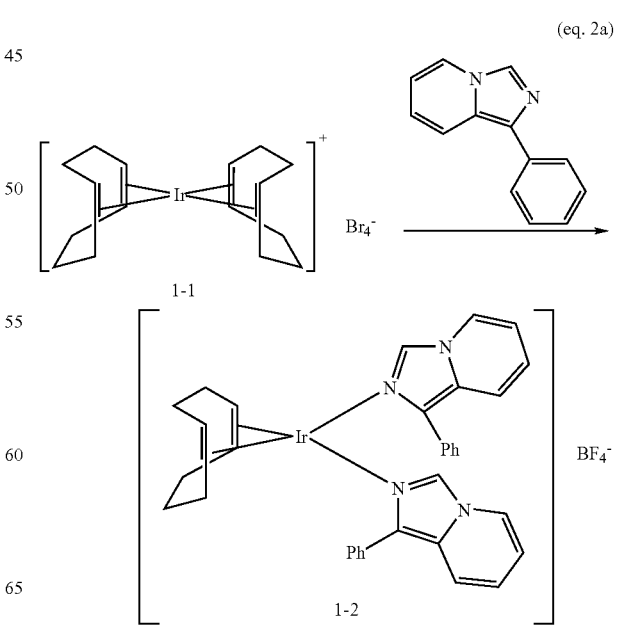

-continued

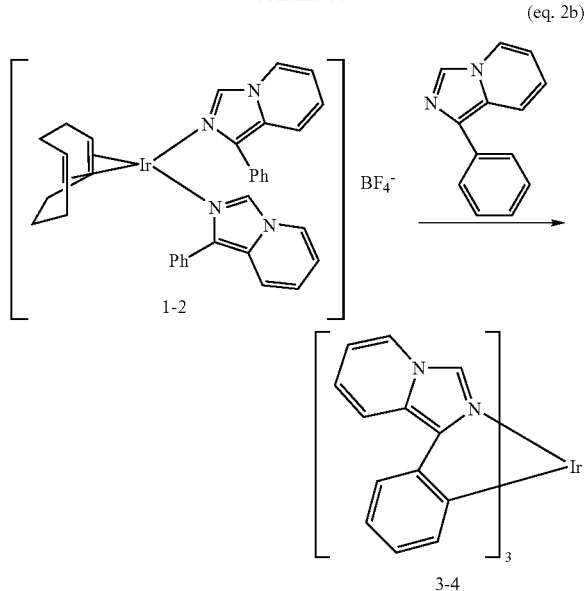

(eq. 2b)

Bis(1,5-cyclooctadiene)iridium(I) tetrafluoroborate (0.7 g, 1.42 mmol) and 1-phenylimidazo[1,2-a]pyridine (1.3 g, 6.7 mmol) were taken up in 1,2-propanediol (15 mL) and the mixture freeze/thaw degassed. The mixture was heated to 80° C. for 20 min. under a nitrogen atmosphere at which point a yellow precipitate formed. The temperature was slowly raised to 160° C. over a period of 2 h. The mixture was cooled to room temperature and the precipitate collected and washed with cold methanol. The solid was dried in vacuo to yield 0.64 g (59%) of bis(1-phenylimidazopyridine)-1,5-cycoloctadiene-iridium(I) tetrafluoroborate (1-2). Analysis by MALDI-TOF mass spectrometry (m/e 689) and by $^1$H-nmr spectroscopy confirmed the structure of this material.

Bis(1-phenylimidazopyridine)-1,5-cycoloctadiene-iridium(I) tetrafluoroborate (1.28 g 1.65 mmol) and 1-phenylimidazopyridine (1.0 g, 5.1 mmol) were taken up in 1,2-propanediol (30 mL) and freeze/thaw degassed. Under a nitrogen atmosphere, the temperature was slowly raised to 50° C. and held for 20 min. The temperature was then increased to 165° C. for 45 min. The precipitate was collected upon cooling and washed with cold methanol to yield 0.8 g (63%, 96% pure by HPLC analysis) of the product. Analysis by MALDI-TOF mass spectrometry (m/e 772) and by $^1$H-nmr spectroscopy confirmed that this material was fac-tris(2-phenylimidazopyridinato-N,C$^{2'}$)iridium(III).

EXAMPLE 3

Preparation of tris-(2-(4',6'-difluoro-phenyl)-5-trifluoromethyl-pyridinato-N,C$^{2'}$)iridium(III) (3-19)

Bis(1,5-cyclooctadiene)iridium(I) tetrafluoroborate (0.7 g, 1.42 mmol) and 2-(4',6'-difluoro-phenyl)-5-trifluoromethyl-pyridine (1.704 g, 7.1 mmol) was placed under nitrogen atmosphere in a 100 mL 2-neck round bottom flask equipped with a reflux condenser. Previously degassed 1,3-butanediol (30 mL) under nitrogen atmosphere was transferred to the reaction flask via cannula. The reaction mixture first turned dark green as it was heated to reflux temperature (202° C.), and then turned orange after heating about 30 min. Reflux was continued 5 h. After cooling, a yellow powder was filtered in air, washed with water, and dried (0.664 g, 97.4% pure by HPLC analysis). This material was sublimed in a tube furnace with nitrogen entrainment gas at 215 C to give the yellow product (0.615 g). Mass spectrometry confirmed the identity of the product as tris-(2-(4',6'-difluoro-phenyl)-5-trifluoromethyl-pyridinato-N,C$^{2'}$)Iridium(III).

EXAMPLE 4

Preparation of fac-bis(1-phenylpyrazolo)(1-phenylimidazopyridine) iridium(III) (3-27)

Bis(1,5-cyclooctadiene)iridium(1+) tetrafluoroborate (0.7 g, 1.42 mmol) and N-phenylpyrazole (0.41 g, 2.8 mmol) were taken up in 1,2-propanediol (15 mL) and the mixture freeze/thaw degassed under nitrogen/vacuum purge. The mixture was heated to 80° C. for 20 minutes under a nitrogen atmosphere at which point a yellow precipitate formed. The precipitate was filtered from the solution and rinsed with diethyl ether. The precipitate was resuspended in 1,2-propanediol (15 mL) and 1-phenylimidazo[1,2-a]pyridine (0.82 g, 4.2 mmol) added. The mixture was freeze-thaw degassed under nitrogen/vacuum purge. The reaction mixture was stirred under nitrogen and the temperature slowly raised to 160° C. over a period of 2 hours. The mixture was cooled to room temperature and the precipitate collected and washed with cold methanol. The solid was dried in vacuo to yield 0.72 g (67%) of the desired product as a yellow solid. The product was purified by flash column chromatography with dichloromethane eluent to yield 0.63 g (66%) of bis(1-phenylpyrazolo)(1-phenylimidazopyridine) iridium(III). The product was further purified by vacuum sublimation. MALDI-TOF—672. The $^1$H nmr spectrum was consistent with the structure of the proposed product.

An alternative preparation of iridium (I)-bis(1-phenylpyrazolo)(1,5-cyclooctadiene) tetrafluoroborate was also developed. Bis(1,5-cyclooctadiene)iridium(1+) tetrafluoroborate (0.7 g, 1.42 mmol) and N-phenylpyrazole (0.41 g, 2.8 mmol) were taken up in dry, degassed dichloromethane (10 mL). The mixture was stirred at room temperature for 10 minutes under a nitrogen atmosphere. Then, anhydrous diethyl ether was added until a yellow precipitate formed. The precipitate was filtered from the solution and rinsed with diethyl ether to yield iridium (I)-bis(1-phenylpyrazolo)(1,5-cyclooctadiene) tetrafluoroborate in 65% yield. This intermediate was suitable for further derivatization as described above.

EXAMPLE 5

Preparation of fac-tris-(2-(4',6'-difluoro-phenyl)-pyridinato-N,C$^{2'}$)iridium(III) (3-24)

Bis(1,5-cyclooctadiene)iridium(I) tetrafluoroborate (1.23 g, 2.48 mmol) and 2-(4',6'-difluoro-phenyl)pyridine (2.4 mL) and 30 mL 1,2-propanediol were placed in a 100 mL round bottom flask equipped with a reflux condenser. The mixture was freeze-thaw degassed, then refluxed under nitrogen for 4 hrs. After cooling, a yellow-green powder was filtered in air, washed with water, and dried (1.40 g). Analysis by HPLC and Mass spectrometry showed the product comprised a mixture of about 92% fac- and 8% mer-tris-(2-(4',6'-difluoro-phenyl)-pyridinato-N,C$^{2'}$)iridium(III). The mixture was extracted with tetrahydrofuran (125 mL) in a Soxhlet extractor under nitrogen. A yellow precipitate in the collection flask was filtered and dried (1.01 g) and found by HPLC to be enriched in content of the facial isomer to about 98% with less than 2% meridional isomer. (Clearly, repeating the Soxhlet extraction procedure would result in even lower levels of meridional isomer in the final product.) This material was further purified by sublimation in a tube furnace with nitrogen entrainment gas at 276° C. to give 0.898 g sublimed fac-tris-(2-(4',6'-difluoro-phenyl)-pyridinato-N,$C^{2'}$)iridium(III). Identity of the product was confirmed by $^1$H nmr spectroscopy.

EXAMPLE 6

Preparation of fac-tris-(2-phenylquinolinato-N,$C^{2'}$) iridium(III) (3-25)

Bis(1,5-cyclooctadiene)iridium(I) tetrafluoroborate (0.603 g, 1.22 mmol), 2-phenylquinoline (1.249 g,) and 30 mL 1,2-propanediol were placed in a 100 mL round bottom flask equipped with a reflux condenser. The mixture was freeze-thaw degassed, then refluxed under nitrogen for 16 hrs. After cooling, a dark red precipitate was filtered in air, washed with ethanol, and dried (0.474 g). The product was identified as fac-tris-(2-phenylquinolinato-N,$C^{2'}$)iridium(III) by $^1$H nmr spectroscopy and mass spectrometry (48.4% yield).

As can be seen from the above examples, the process provides a simple method to prepare tris-cyclometallated metal complexes in good yield and purity. The tris-cyclometallated metal complexes synthesized according to this invention may be incorporated in an EL device. In one embodiment the tris-cyclometallated metal complexes are included in a light-emitting layer of an EL device.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

The invention claimed is:

1. A process for forming a tris-cyclometallated complex comprising the step of reacting;
   a) an M(I) complex, wherein M represents Rh or Ir, and said complex comprises at least two ligands and contains at least two alkenyl groups pi-bonded to M, wherein the M(I) complex is represented by Formula (1):

$[(L^1)_n M(L^2)_m]X$     (1)

wherein:
   M represents Ir(I) or Rh(I);
   each $L^1$ represents an independently selected ligand comprising an alkenyl group and provided that two $L^1$ groups may join to form a diene or cyclodiene group;
   each $L^2$ represents an independently selected Lewis base ligand;
   n is 2-4;
   m is 0-2;
   the sum of m and n is 4; and
   X represents a counterion with
   b) a heterocyclic compound capable of forming a organometallic cyclometallated complex.

2. The process according to claim 1, wherein M represents Ir.

3. The process according to claim 1, wherein the two alkenyl groups comprise a cyclodiene group.

4. The process according to claim 3, wherein the cyclodiene group comprises a 1,5-cyclooctadiene group.

5. The process according to claim 1, wherein the M(I) complex includes at least four alkenyl groups pi-bonded to M.

6. The process according to claim 5, wherein the four alkenyl groups comprise two independently selected cyclodiene groups.

7. The process according to claim 1, wherein the M(I) complex includes two monodentate ligands.

8. The process according to claim 7, wherein at least one monodentate ligand is coordinated to the metal by means of a nitrogen-metal bond or an oxygen-metal bond.

9. A process according to claim 1, wherein the heterocyclic compound comprises at least two heteroatoms.

10. A process according to claim 1, wherein the heterocyclic compound comprises a pyridine group, a quinoline group, an isoquinoline group, a pyrimidine group, an indole group, an indazole group, a thiazole group, an oxazole group, an imidazole group, or a pyrazole group.

11. A process according to claim 1, wherein the tris-cyclometallated complex formed comprises at least 95% of the facial isomer.

12. A process according to claim 1, further comprising a diol solvent.

13. A process according to claim 1, wherein, n is 2, m is 2, and the two $L^1$ groups join to form a cyclodiene group, each $L^2$ represents an independently selected monodentate ligand.

14. A process according to claim 1, wherein n is 4, m is 0 and the $L^1$ groups join together so as to form two independently selected cyclodiene groups.

15. A process according to claim 1 wherein the heterocycle is represented by Formula (2a):

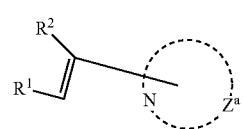

(2a)

wherein:
$Z^a$ represents the atoms necessary to form a an aromatic ring group; and
$R^1$ and $R^2$ represent substituent groups, provided that $R^1$ and $R^2$ may form a ring group.

16. A process according to claim 1 wherein the heterocycle is represented by Formula (2b):

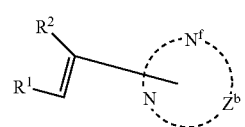

(2b)

wherein:
Z represents the atoms necessary to form a diazole ring group that is fused with at least one aromatic ring group;
$N^f$ represents a nitrogen atom at a bridgehead position between the diazole ring group and the fused aromatic ring group; and
$R^1$ and $R^2$ represent substituent groups, provided that $R^1$ and $R^2$ may form a ring group.

17. A process according to claim 1 wherein the tris-cyclometallated complex is represented by Formula (3b):

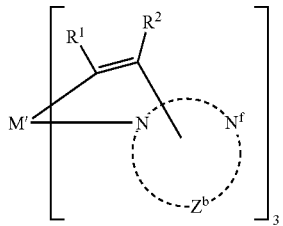

wherein:

Z represents the atoms necessary to form a diazole ring group that is fused with at least one aromatic ring group;

$N^f$ represents a nitrogen atom at a bridgehead position between the diazole ring group and the fused aromatic ring group;

M' represents Ir(III) or Rh(III); and $R^1$ and $R^2$ represent substituent groups, provided that $R^1$ and $R^2$ may form a ring group.

18. A process according to claim 1 wherein the tris-cyclometallated complex is represented by Formula (3c):

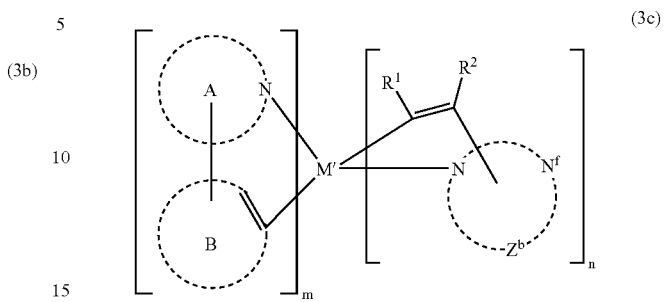

wherein:

Z represents the atoms necessary to form a diazole ring group that is fused with at least one aromatic ring group;

$N^f$ represents a nitrogen atom at a bridgehead position between the diazole ring group and the fused aromatic ring group;

M' represents Ir(III) or Rh(III);

$R^1$ and $R^2$ represent substituent groups, provided that $R^1$ and $R^2$ may form a ring group;

A represents a substituted or unsubstituted heterocyclic ring group containing at least one nitrogen atom;

B represents a substituted or unsubstituted aromatic or heteroaromatic ring;

m is an integer from 1 to 3; and n in an integer from 0 to 2 such that m+n=3.

19. A process according to claim 1 wherein the reaction is heated to a temperature in the range of 140-190° C.

20. A process according to claim 1, wherein, n is 2, m is 2, and the two $L^2$ groups join to form a neutral bidentate ligand.

* * * * *